(12) United States Patent
Hardin et al.

(10) Patent No.: US 6,976,955 B2
(45) Date of Patent: Dec. 20, 2005

(54) HANDLE FOR MEDICAL DEVICES, AND MEDICAL DEVICE ASSEMBLIES INCLUDING A HANDLE

(75) Inventors: David M. Hardin, Winston-Salem, NC (US); Jason D. Foushee, Winston-Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 0 days.

(21) Appl. No.: 10/699,487

(22) Filed: Oct. 31, 2003

(65) Prior Publication Data
US 2004/0260274 A1   Dec. 23, 2004

Related U.S. Application Data

(60) Provisional application No. 60/479,709, filed on Jun. 19, 2003.

(51) Int. Cl.[7] ................................................. A61B 1/00
(52) U.S. Cl. ..................... 600/131; 604/528; 604/529
(58) Field of Search ................. 600/131; 604/528–529

(56) References Cited

U.S. PATENT DOCUMENTS

| | | | |
|---|---|---|---|
| 3,613,664 A | 10/1971 | Wilson et al. | |
| 5,127,419 A | 7/1992 | Kaldany | |
| 5,611,778 A * | 3/1997 | Brinon ........................ | 604/117 |
| 5,683,413 A | 11/1997 | Miyagi | |
| 6,283,951 B1 * | 9/2001 | Flaherty et al. ............. | 604/529 |
| 6,423,074 B1 | 7/2002 | Chen | |
| 6,524,259 B2 * | 2/2003 | Baxter-Jones et al. ...... | 600/591 |
| 6,579,279 B1 * | 6/2003 | Rabiner et al. ............. | 604/528 |
| 2002/0002349 A1 | 1/2002 | Flaherty et al. | |

FOREIGN PATENT DOCUMENTS

| EP | 0 410 561 A1 | 4/1990 |
|---|---|---|
| EP | 0 738 501 A1 | 2/1995 |
| WO | WO 96/39077 | 12/1996 |

* cited by examiner

Primary Examiner—Beverly M. Flanagan
Assistant Examiner—Matthew J. Kasztejna
(74) Attorney, Agent, or Firm—Brinks Hofer Gilson & Lione

(57) ABSTRACT

A handle for a medical device is provided. The handle includes an inner handle member and first and second outer handle members slideably disposed on the inner handle member. An elongate sheath is attached to the inner handle member and extends axially beyond a distal end of the inner handle member and a stylet is attached to one of the outer handle members and disposed in a lumen of the sheath. Slideable movement of the outer handle members relative to the inner handle members controls relative positioning of various components of the handle.

29 Claims, 12 Drawing Sheets

HANDLE FOR MEDICAL DEVICES, AND MEDICAL DEVICE ASSEMBLIES INCLUDING A HANDLE

REFERENCE TO PREVIOUS APPLICATION

This application claims the benefit of U.S. provisional application Ser. No. 60/479,709, filed on Jun. 19, 2003.

FIELD OF THE INVENTION

The invention relates generally to the field of medical devices. More specifically, the invention relates to handles for use with other medical devices, combinations of handles and other medical devices, methods of making such handles and medical devices, and methods of using such handles and medical devices.

BACKGROUND OF THE INVENTION

The development of minimally invasive methods and devices over recent years has revolutionized the practice of medicine. These methods and devices allow clinicians to perform a wide variety of procedures while minimizing trauma to the patient. A wide variety of treatment devices that utilize minimally invasive technologies has been developed, and includes stents, stent grafts, occlusion devices, perfusion catheters, drainage catheters, drug delivery systems and endoscopes.

In many minimally invasive devices, a sheath surrounds an inner component, such as a stylet or trocar. Together, these components are navigated through a body lumen to a point of treatment. Once this point is reached, the clinician may need to manipulate these and other components relative to each other to achieve the goal of the treatment. For example, the clinician may need to move a sheath relative to an inner trocar to allow sampling of a tissue for a biopsy.

In these techniques and devices, it is important to have an ability to control this relative movement in the components. For example, if a trocar has a sharp edge, it may be necessary to maintain a sheath over the trocar during navigation. Also, it may prove beneficial to have control over the precise length by which an inner component, such as a trocar, extends distantly beyond another component, such as a sheath.

In some procedures, several components, such as a sheath and a trocar, are used in combination with another medical device, such as an endoscope. In these procedures it may prove helpful to control the amount by which the sheath extends beyond a distal end of the endoscope.

BRIEF SUMMARY OF THE INVENTION

The present invention provides a handle for use with other medical devices. In one embodiment, a handle according to the invention comprises an inner handle member having proximal and distal ends, a first outer handle member slideably disposed on the proximal end, and a second outer handle member slideably disposed on the distal end of the inner handle member. An elongate sheath defines a sheath lumen and is attached to the inner handle member. The elongate sheath extends axially beyond the distal end of the inner handle member. A stylet is attached to the first outer handle member and disposed in the sheath lumen.

In another embodiment, a handle according to the invention comprises an inner handle member and first and second outer handle members slideably disposed on the inner handle member. An elongate sheath is attached to the inner handle member and defines a sheath lumen. A stylet is attached to the first outer handle member and disposed in the sheath lumen. A series of gradations is disposed on the inner handle member. Each gradation corresponds to a predetermined length by which the stylet extends axially beyond a distal end of the sheath.

In another embodiment, a handle according to the invention comprises an inner handle member having proximal and distal ends and defining a handle lumen, a first outer handle member slideably disposed of the proximal end of the inner handle member, and a second outer handle member slideably disposed on the distal end of the inner handle member. An elongate sheath is attached to the inner handle member, extends axially beyond the distal end of the inner handle member, and defines a sheath lumen. A stylet is attached to the first outer handle member and extends through the handle lumen and into the sheath lumen. First and second series of gradations are disposed on the inner handle member. Each gradation of the first series of gradations corresponds to a predetermined length by which the stylet extends axially beyond a distal end of the sheath. Each gradation of the second series of gradations corresponds to a predetermined length by which the sheath extends axially beyond a distal end of the second outer handle member.

The invention also provides various medical device assemblies that include a medical device and a handle according to the invention attached to the medical device. In one embodiment, a medical device assembly according to the invention comprises a medical device defining a working lumen and a handle attached to the medical device. The handle comprises an inner handle member having proximal and distal ends, a first outer handle member slideably disposed on the proximal end of the inner handle member, and a second outer handle member slideably disposed on the distal end of the inner handle member. The second outer handle member is connected to the medical device. An elongate sheath is attached to the inner handle member and axially extends beyond the distal end of the inner handle member and into the working lumen of the medical device. The elongate sheath defines a sheath lumen. A stylet is attached to the first outer handle member and disposed in the sheath lumen.

In one embodiment of a medical device assembly according to the invention, the medical device comprises an endoscope.

BRIEF DESCRIPTION OF SEVERAL VIEWS OF THE DRAWINGS

FIG. 7A is a sectional view of the handle illustrated in FIG. 7 taken along long line 7A—7A.

DETAILED DESCRIPTION OF EXEMPLARY EMBODIMENTS OF THE INVENTION

Figure 1:
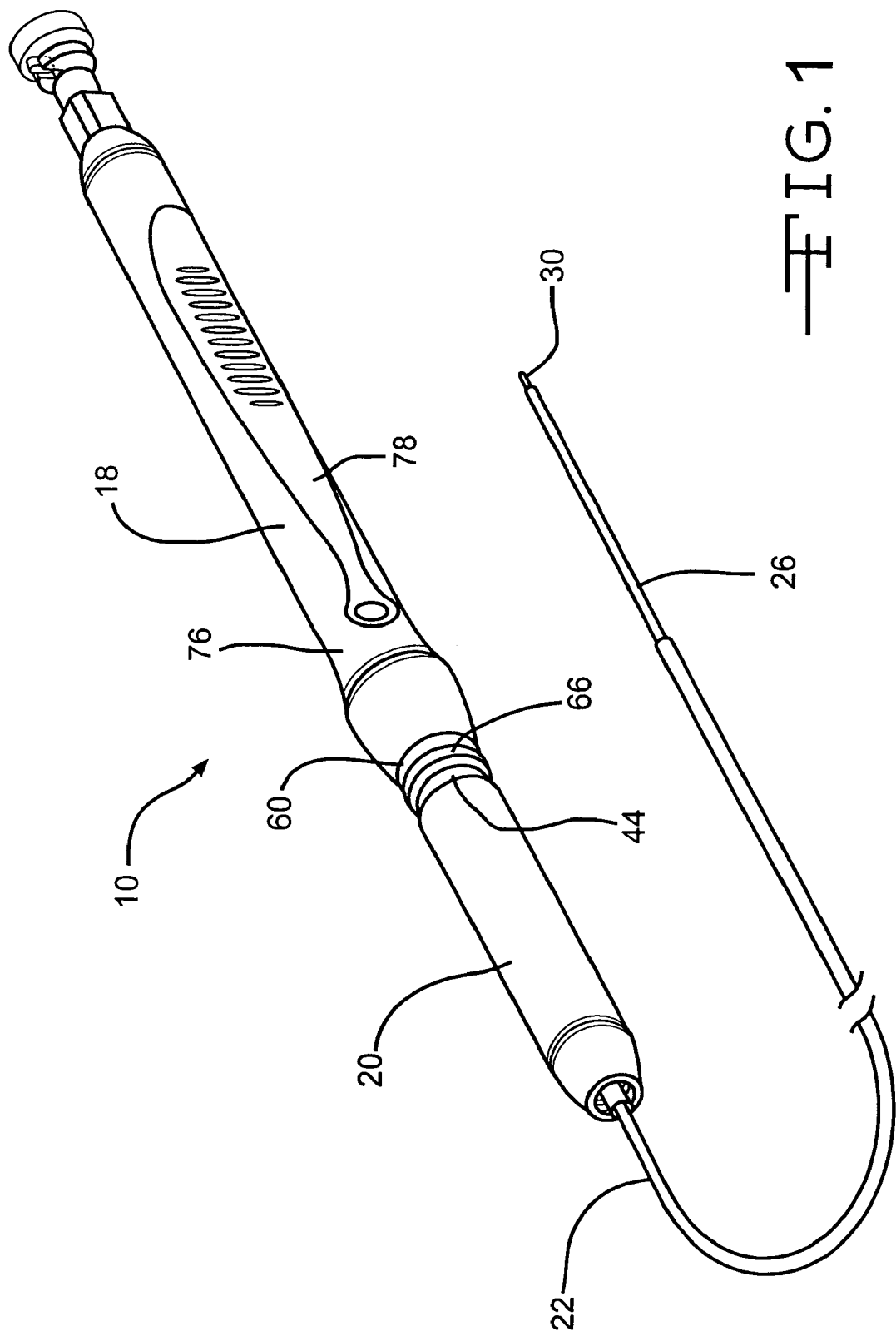
FIG. 1 is a perspective view of a handle according to one embodiment of the invention.

The following provides a detailed description of several embodiments of the invention. The embodiments described and illustrated herein are exemplary in nature, and are not intended to limit the scope of the invention in any matter. Rather, the description of these embodiments serves simply to aid in enabling one of ordinary skilled in the art to make and use the invention.

FIGS. 1–3, 3A, 3B, 4, 4A, and 4B illustrate a handle 10 for a medical device according to one embodiment of the invention. In this embodiment, the handle 10 comprises an inner handle member 12 having proximal 14 and distal 16 ends. A first outer handle member 18 is slideably disposed on the proximal end 14 of the inner handle member 12. A second outer handle member 20 is slideably disposed on the distal end 16 of the inner handle member. An elongate sheath 22 is attached to the inner handle member 12 and extends axially beyond the distal end 16 of the inner handle member 12. As used herein, the term "axially" refers to one member situated around, in the direction of, on, or along an axis of another member, and is not limited to one member situated around, in the direction of, on, or along a central axis of another member. The sheath 22 defines a sheath lumen 24. A stylet 26 is attached to the first outer handle member 18 and is at least partially disposed in the sheath lumen 24. The stylet 26 can define a stylet lumen 28, and a trocar 30 can be disposed in the stylet lumen 28. If present, the trocar 28 can extend axially beyond the second outer handle member, and into the sheath lumen 24.

FIG. 1 illustrates the handle 10 according to this embodiment of the invention in a closed configuration. That is, the first 18 and second 20 outer handle members are advanced fully onto their respective portions of the inner handle member 12. In this configuration of this embodiment, the first 18 and second 20 outer handle members envelop the inner handle member 12.

Figure 2:
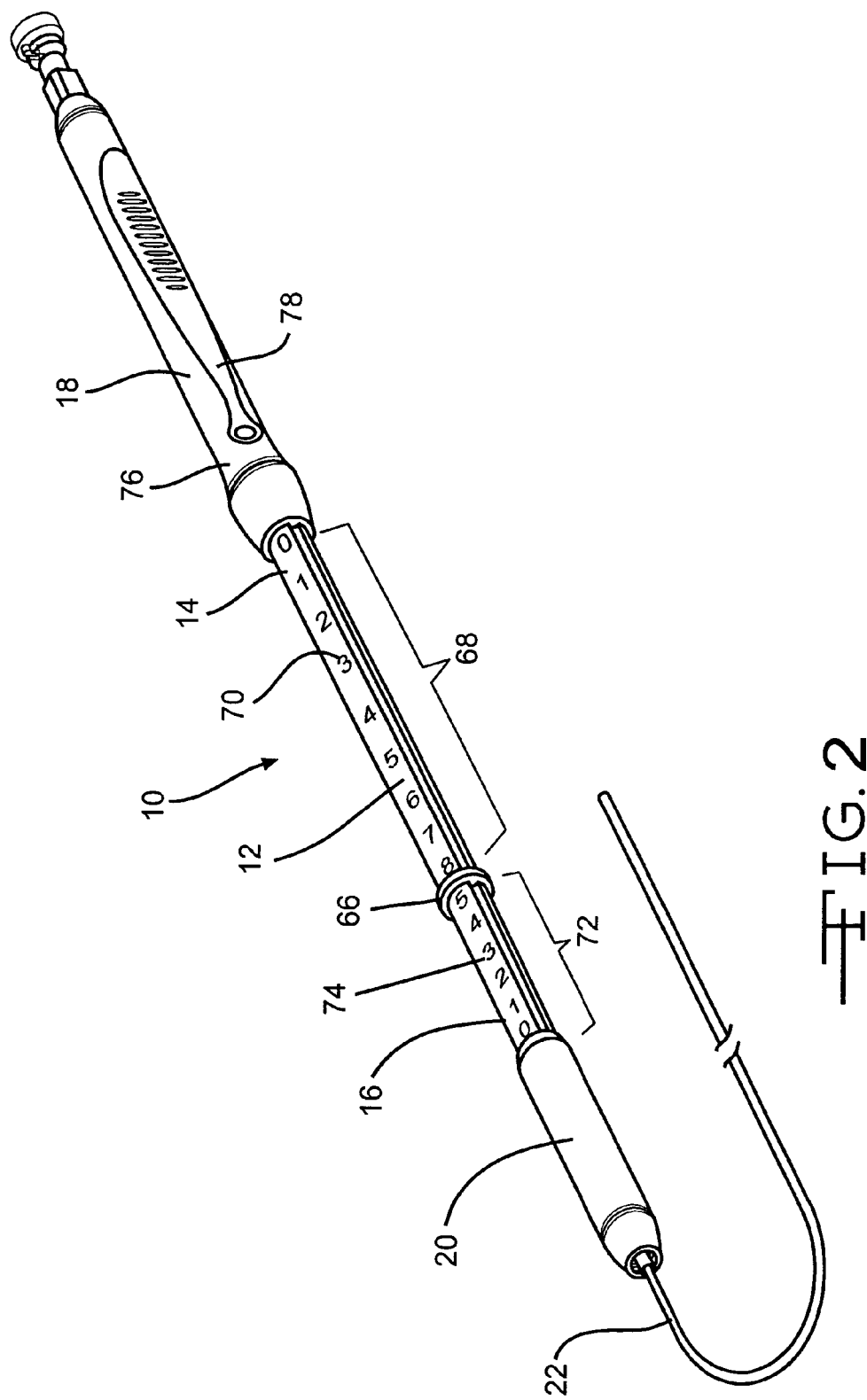
FIG. 2 is a perspective view of the handle illustrated in FIG. 1 shown in an open configuration.

FIG. 2 illustrates the handle 10 in an open configuration. In this configuration, both the first 18 and second 20 outer handle members are retracted from their respective positions relative to the inner handle member illustrated in FIG. 1. This open configuration reveals the inner handle member 12. Changing the handle 10 from the closed configuration illustrated in FIG. 1 to the open configuration illustrated in FIG. 2 results in different relative positions of various components. For example, because the sheath 22 is attached to the inner handle member 12, movement of the second outer handle member 20 along the inner handle member 12 changes the length by which the sheath 22 extends axially beyond the distal end of the second outer handle member 20. Also, because the stylet 26 is attached to the first outer handle member 18, movement of the first outer handle member 18 along the inner handle member 12 changes the position of the stylet 26 relative to the sheath 22. Some of this movement may change a length by which the stylet 26 extends axially beyond a distal end of the sheath 22. A comparison of FIGS. 1 and 2 illustrates that the stylet 26 may extend axially beyond a distal end of the sheath 22 when the handle 10 is in a closed configuration (FIG. 1), but may be completely within the sheath 22 when the handle is in an open configuration (FIG. 2).

Figure 3:
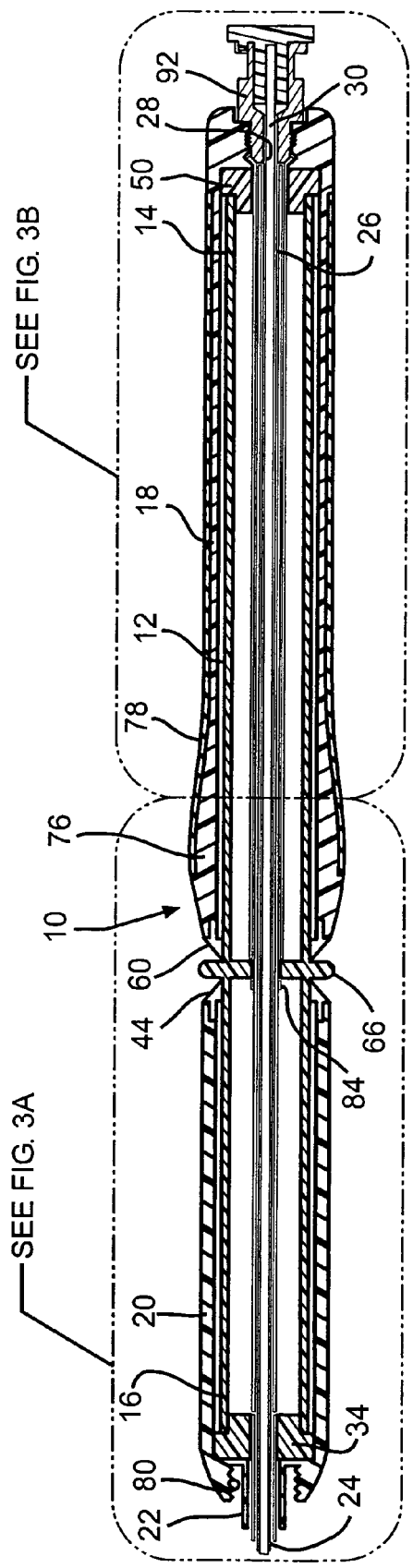
FIG. 3 is a longitudinal sectional view of the handle illustrated in FIG. 1.
Figure 3A:
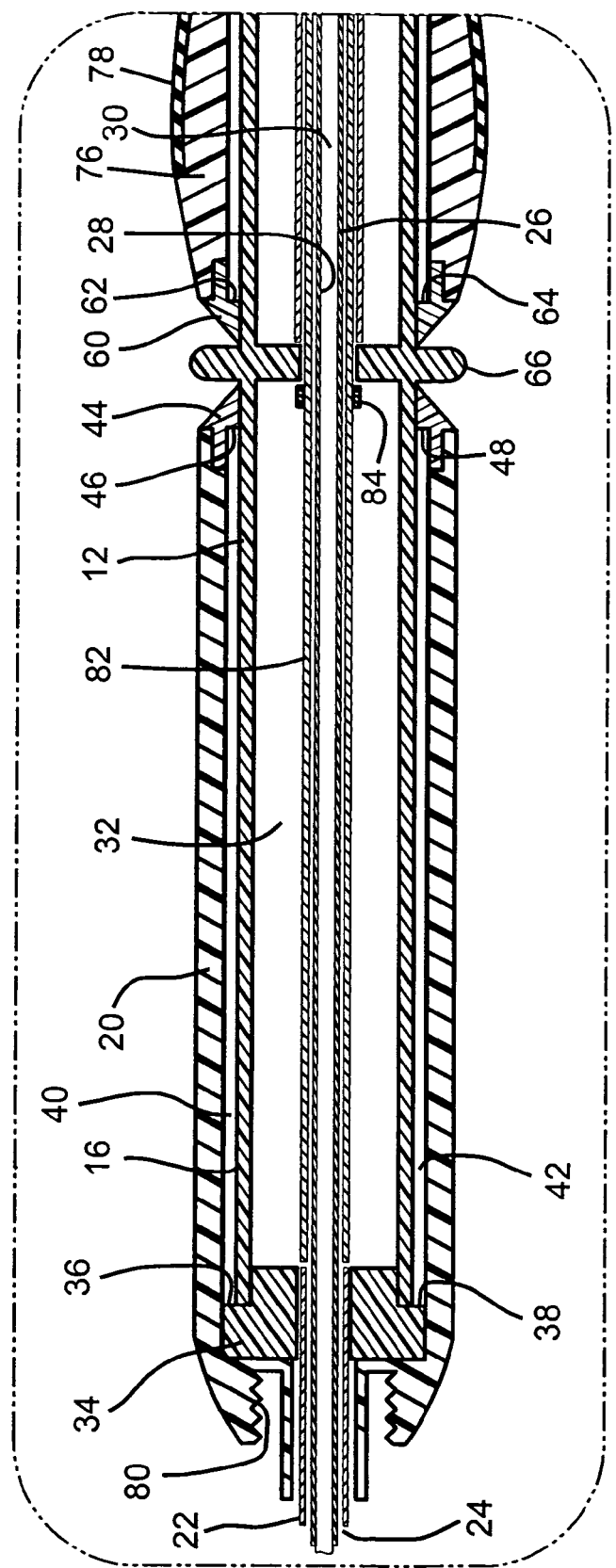
FIG. 3A is a magnified view of a first portion of the handle illustrated in FIG. 3.
Figure 3B:
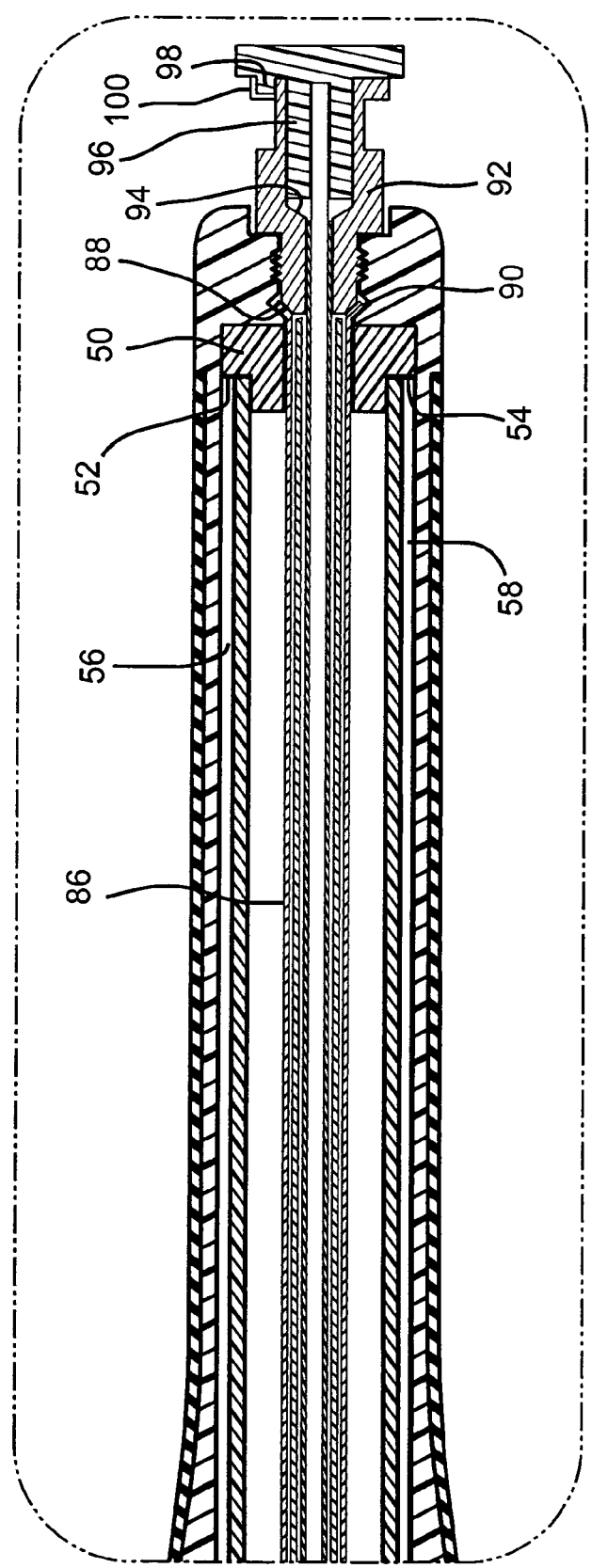
FIG. 3B is a magnified view of a second portion of the handle illustrated in FIG. 3.
Figure 4:
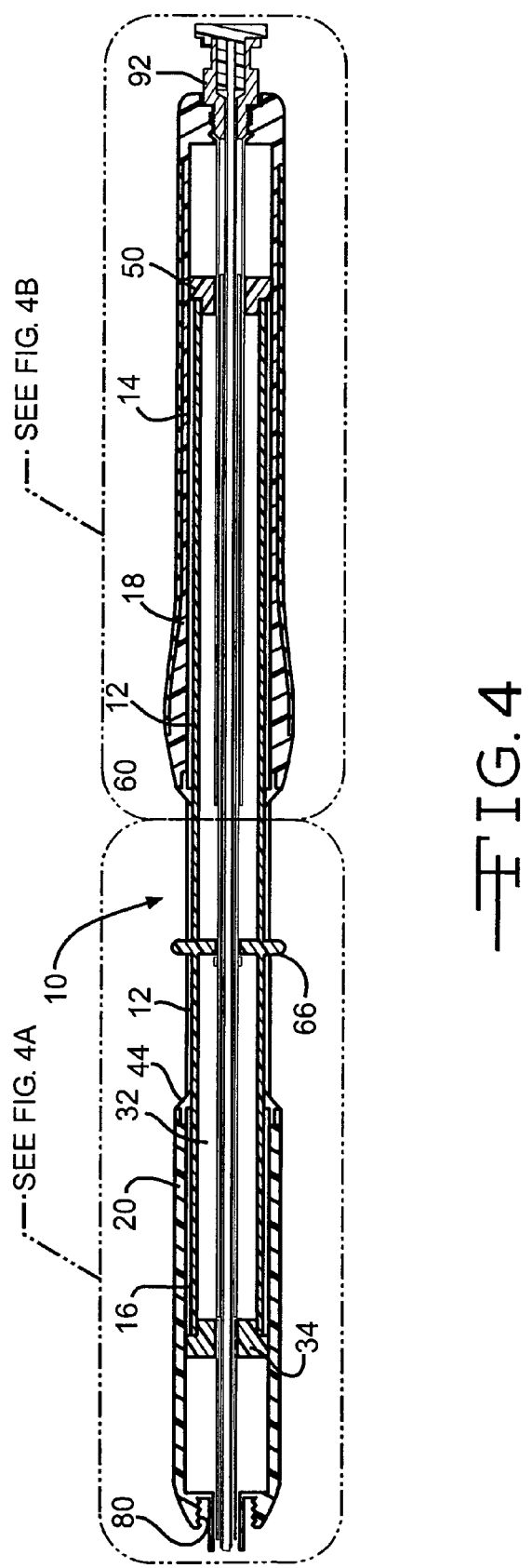
FIG. 4 is a longitudinal sectional view of the handle illustrated in FIG. 2.
Figure 4A:
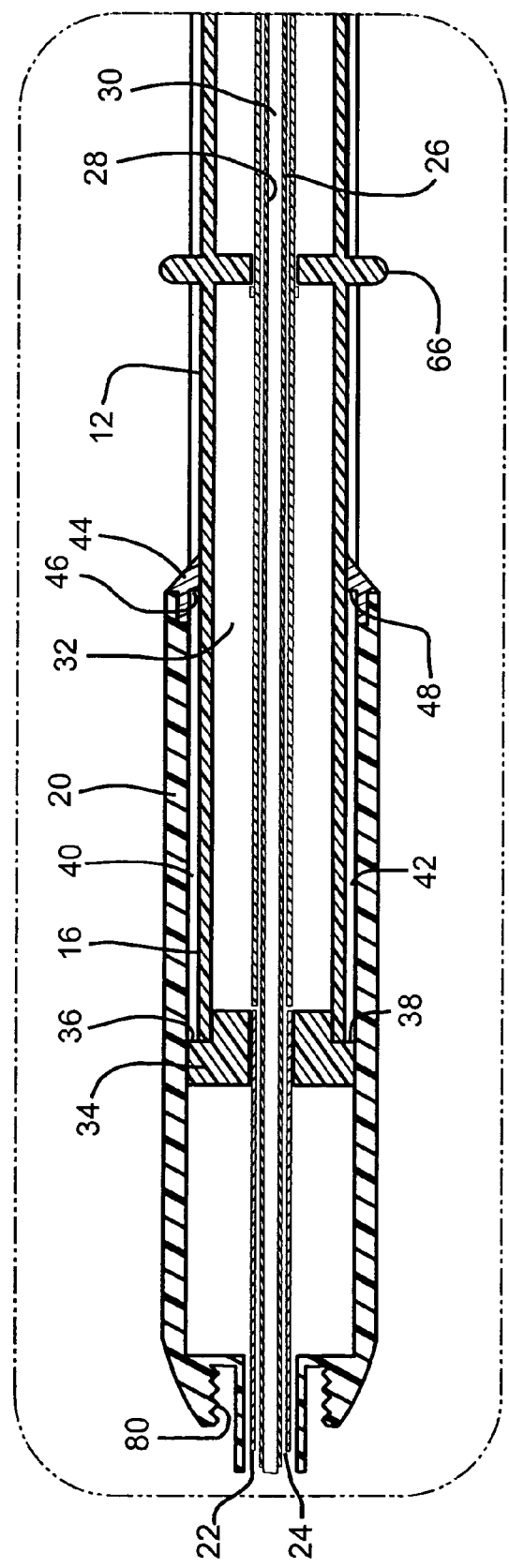
FIG. 4A is a magnified view of a first portion of the handle illustrated in FIG. 4.
Figure 4B:
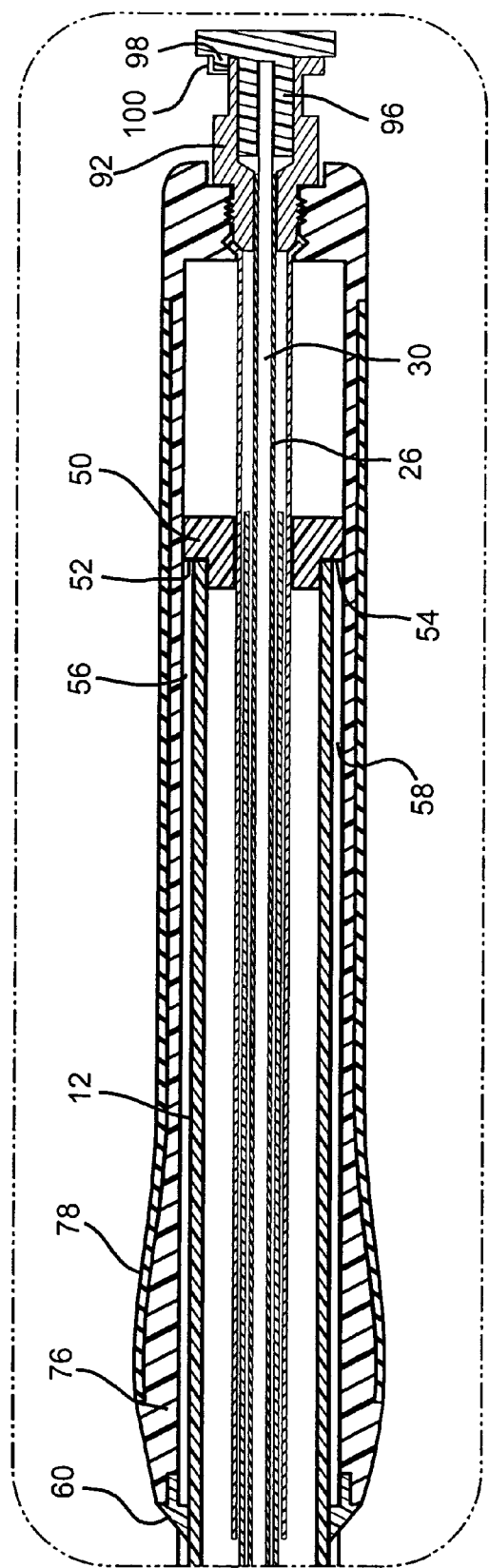
FIG. 4B is a magnified view of a second portion of the handle illustrated in FIG. 4.

FIGS. 3 and 4 illustrate sectional views of the handle 10 in closed and open configurations, respectively. Together with the magnified views presented in FIGS. 3A, 3B, 4A and 4B, these figures illustrate the various mechanisms by which the handle 10 controls the relative positioning of the various components.

The inner handle member 12 defines a handle lumen 32 that contains various portions of various components of the handle 10. A distal cap 34 closes the handle lumen 32 at the distal end 16 of the inner handle member 12. The distal cap 34 can comprise an integral portion of the inner handle member 12 or can be a separately attached member. The distal cap 34 defines first 36 and second 38 distal cap stops. These stops 36, 38 are positioned at ends of first 40 and second 42 distal races defined by the inner handle member 12. The second outer handle member 20 includes a distal collar 44 that defines first 46 and second 48 projections. These projections 46, 48 move along the first 40 and second 42 distal races, respectively, as the second outer handle member 20 is slideably moved along the inner handle member 12. Eventually, the distal cap stops 36, 38 abut projections 46, 48 to prevent further distal movement of the second outer handle member 20. As with the distal cap 34, the distal collar 44 can comprise an integral component of the second outer handle member 20 or can be a separately attached member. Further, the inner handle member 12 can include a lesser or greater number of distal races, or the handle 10 generally can include any suitable alternative mechanism for limiting movement of the second outer handle member 20 along the inner handle member 12.

A proximal cap 50 closes the handle lumen 32 at the proximal end 14 of the inner handle member 12. The proximal cap 50 defines first 52 and second 54 proximal cap stops. These stops 52, 54 are positioned at ends of first 56 and second 58 proximal races defined by the inner handle member 12. The first outer handle member 18 includes a proximal collar 60 that defines first 62 and second 64 projections. These projections 62, 64 move along the first 56 and second 58 proximal races, respectively, as the first outer handle member 18 is slideably moved along the inner handle member 12. Eventually, the proximal cap stops 52, 54 abut projections 62, 64 to prevent further proximal movement of the first outer handle member 18. As with the distal cap 34 and collar 44, the proximal cap 50 and collar 60 can each comprises an integral component of the inner handle member 12 and the first outer handle member 18, respectively, or can be separate members attached to these components. Further, the inner handle member 12 can include a lesser or greater number of proximal races, or the handle 10 generally can include any suitable alternative mechanism for limiting movement of the first outer handle member 18 along the inner handle member 12.

The inner handle member 12 can also include a stop 66 disposed between the first 18 and second 20 outer handle members. The stop 66 separates the areas of the inner handle member 12 along which the first 18 and second 20 outer handle members can be moved. Further, the stop 66 provides a physical barrier to further movement of the outer handle members 18, 20 along the inner handle member 12. If present, the stop 66 can comprise and integral portion of the inner handle member 12, or can be a separately attached member. As best illustrated in FIG. 2, this stop can comprise a circumferential projection defined by the inner handle member 12.

The handle 10 can further include various adaptations to facilitate operation of the handle 10. For example, as best illustrated in FIG. 2, a first series 68 of gradations 70 can be disposed on the inner handle member 12. If present, this series 68 can be disposed on a portion of the inner handle member 12 along which the first outer handle member 18 is moved. In this configuration, each gradation 70 of the series 68 can correspond to a predetermined position of the stylet 26, which is attached to the first outer handle member 18, relative to a distal end of the sheath 22, which is attached to the inner handle member 12. Further, each gradation 70 of this series 68 can correspond to a predetermined length by which the stylet 26 extends axially beyond a distal end of the sheath 22.

A further comparison of FIGS. 1 and 2 illustrates an example of the operation of this series 68 of gradations 70. In the open configuration illustrated in FIG. 2, the proximal most gradation viewable in the series 68 is "0". Also in this configuration, the stylet 26 does not extend beyond the distal end of the sheath 22. Thus, in this example, the gradation "0" can correspond to a zero length of the stylet 26 that extends axially beyond a distal end of the sheath 22. In FIG. 1, the handle is in a completely closed configuration. To achieve this configuration from the open configuration illustrated in FIG. 2, a user would advance the first outer handle member 18 over the entire series 68 of gradations 70. As the user moves the first outer handle member 18 along the inner handle member 12, the first outer handle member 18 successively passes gradations 70 of the series 68. Each gradation 70 can correspond to a length by which the stylet 26 extends beyond a distal end of the sheath 22. Once the first outer handle member 18 is fully advance over the inner handle member 12, reaching stop 66, the entire series 68 of gradations 70 is covered. As illustrated in FIG. 1, this can correspond to a maximum length by which the stylet 26 extends beyond the distal end of the sheath 22. Thus, by moving a distal end of the first outer handle member 18, such as collar 60, to a specific gradation 70 in the series 68, a user of the handle 10 can advance the stylet 26 to a desired position relative to the sheath 22.

The handle 10 can also include a second series 72 of gradations 74. Similar to the first series 68, the second series 72 of gradations 74 can be disposed on the inner handle member 12. The second series 72 can be disposed on a portion of the inner handle member 12 along which the second outer handle member 20 is moved. In this configuration, each gradation 74 of the second series 72 can correspond to a predetermined length by which the sheath 22, which is attached to the inner handle member 12, extends axially beyond a distal end of the second outer handle member 20, which can be attached to another medical device.

A further comparison of FIGS. 1 and 2 illustrates an example of the operation of this series 72 of gradations 74. In the open configuration illustrated in FIG. 2, the proximal most gradation viewable in the series 72 is "0". The gradation "0" can refer to a particular length by which the sheath 22 extends beyond a distal end of the second outer handle member 20. If the second outer handle member 20, and thus the entire handle 10, is used with another medical device having a working lumen, such as an endoscope, the gradation "0" can correspond to a zero length of the sheath 22 that extends axially beyond a distal end of the other medical device. For example, the "0" gradation may indicate that no portion of the sheath 22 extends out of the working lumen of the attached medical device. The second outer handle member 20 passes successive gradations 74 in the series 72 as it is moved along the inner handle member 12. Each gradation 74 in the series 72 can correspond to a predetermined length by which the sheath 22 extends beyond a distal end of the second outer handle member 20. Further, if the second outer handle member 20 is used with another medical device, each gradation 74 can correspond to a predetermined length by which the sheath extends axially beyond a distal end of the medical device. Once the second outer handle member 20 is fully advanced over the inner handle member 12, reaching stop 66 and the closed configuration illustrated in FIG. 1, the entire series 72 of gradations 74 is covered, which can indicate a maximum length by which the sheath 22 extends axially beyond the distal end of the second outer handle member 20 or a distal end of an attached medical device.

The first outer handle member 18 can include structural adaptations that facilitate operation of the handle 10. For example, the first outer handle member 18 can define an enlargement 76 that provides a resting position for a finger or thumb of the user. The enlargement 76 represent a circumferential portion of the first outer handle member 18 that has a larger outer diameter than another portion of the first outer handle member 18. Further, a grip insert 78 can be attached to or defined by the first outer handle member 18. The grip insert 78 provides a surface that facilitates handling of the handle 10. The grip insert 78 can be formed of the same material as the first outer handle member 18, such as a plastic, or can comprise a different material, such as a rubber or other polymeric material.

The handle 10 can be used with other medical devices. In some embodiments, it may be desirable to allow attachment of the handle 10 to another medical device. The second outer handle member 20 can define structural adaptations that facilitate attachment of the handle 10 to another medical device. For example, the second outer handle member 20 can define a connector 80. The connector 80 is structurally capable of interacting with another connector on the other medical device to which the handle 10 is to be attached. This interaction between the connector 80 and the other connector on the medical device can be a mating connection, and can be a locking connection. Any suitable connector can be used as the connector 80, and a Luer-type connector is an example of a particularly well suited connector. Other suitable types of connectors include clamp connectors and engagement member connections, such as thumb screws and the like.

The handle 10 can include additional components that facilitate the relative movement of the interior components of the device. Examples of such additional components are illustrated in FIGS. 3A, 3B, 4A, and 4B. An inner guide tube 82 can be disposed in the handle lumen 32 and around the stylet 26. The inner guide tube 82 is a tubular member that surrounds the stylet 26. The inner guide tube 82 can define a collar 84 disposed near the stop 66 of the inner handle member 12. The inner guide tube 82 can be attached to the inner handle member 12. Also, as best illustrated in FIG. 3A, the position of the inner handle member 12 can be fixed by its surrounding the stylet 26, the positioning of the collar 84 adjacent the stop 66, or both. As best illustrated in FIG. 3B, an outer guide tube 86 can also be disposed in the handle lumen 82 and around a portion of the inner guide tube 82. In this embodiment, the outer guide tube 82 is attached to the first outer handle member 18 and, therefore, slideably moves along the inner guide tube 82 as the first outer handle member 18 is slideably moved along the inner handle member 12. The attachment of the outer guide tube 86 to the first outer handle member 18 can be accomplished in any suitable manner. In this embodiment, the outer guide tube 86 defines a flare 88 at a proximal end. The flare 88 is disposed in a recess 90 of the first outer handle member 18. An access port 92 is positioned at a proximal end of the first outer handle member 18 and adjacent the flare 88, effectively locking the outer guide tube 86 in position relative to the first outer handle member 18. This attachment can also include an adhesive or other suitable bonding mechanism.

The inclusion of inner 82 and outer 86 guide tubes may prevent buckling of components within the handle lumen 32 during repetitive movement of the handle 10 between open and closed configurations.

The access port 92 provides access to the stylet lumen 28 from an environment external to the handle 10. The access port 92 can be integrally formed by the first outer handle member 18 or can comprise a separately attached member. The access port 92, if included, need only provide the desired access to the stylet lumen 28.

If present, the trocar 30 can be slideably disposed in access port 92. The trocar 30 can define or include a cap 96 that facilitates its insertion into and removal from the access port 92. The cap 96 can interact with a throat 94 defined by the access port 92 to guide and/or limit the movement of the trocar 30 into the access port 92. Further, the cap 96 can define structural adaptations that fix the position of the cap 96 relative to the access port 92. For example, the cap 96 can define a notch 98 that is received by a slot 100 defined by the access port 92. This interaction between the notch 98 and the slot 100 prevents rotational movement of the cap 96 and the attached trocar 30.

Figure 5:
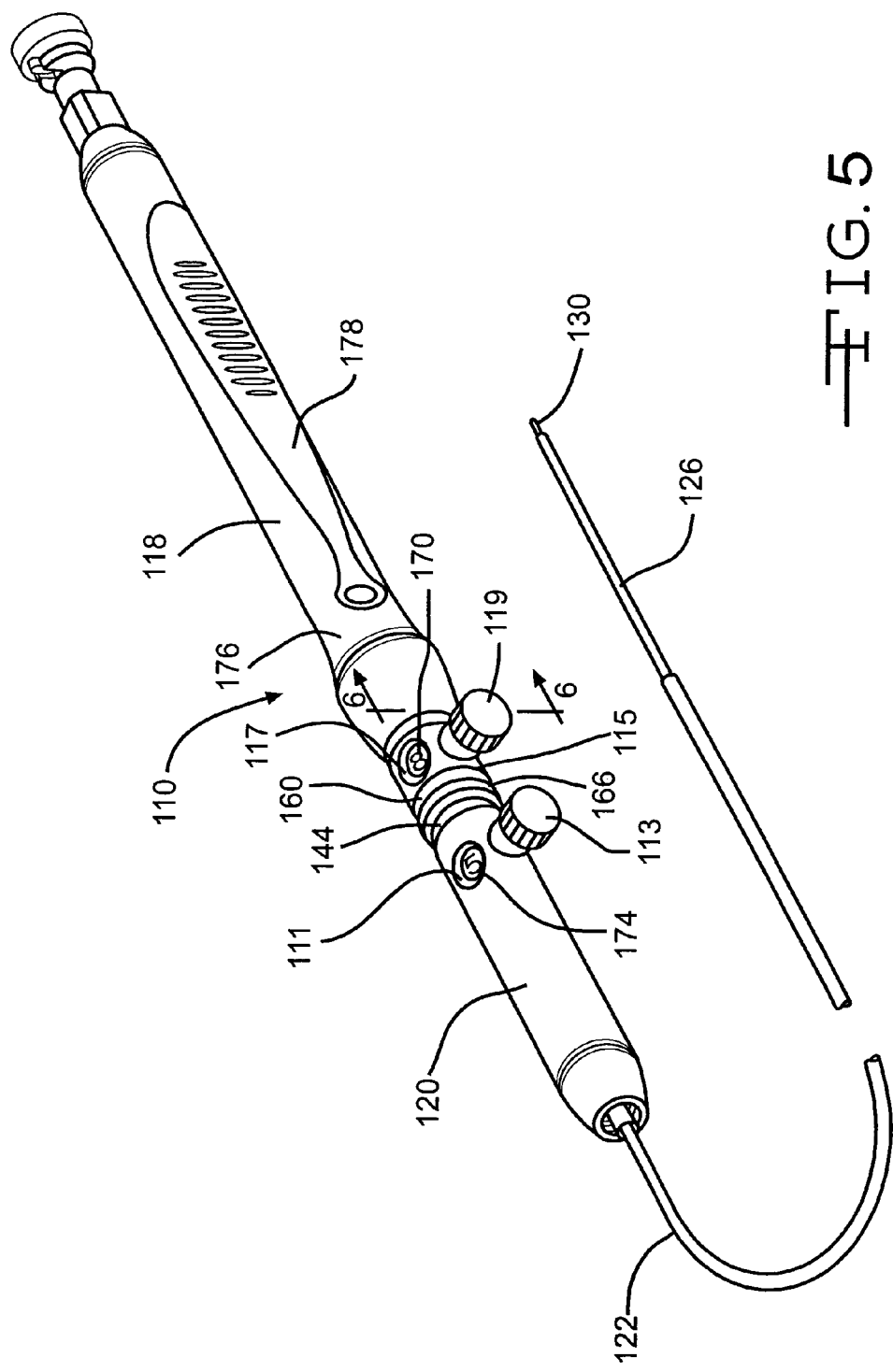
FIG. 5 is a perspective view of a handle according to another embodiment of the invention.
Figure 6:
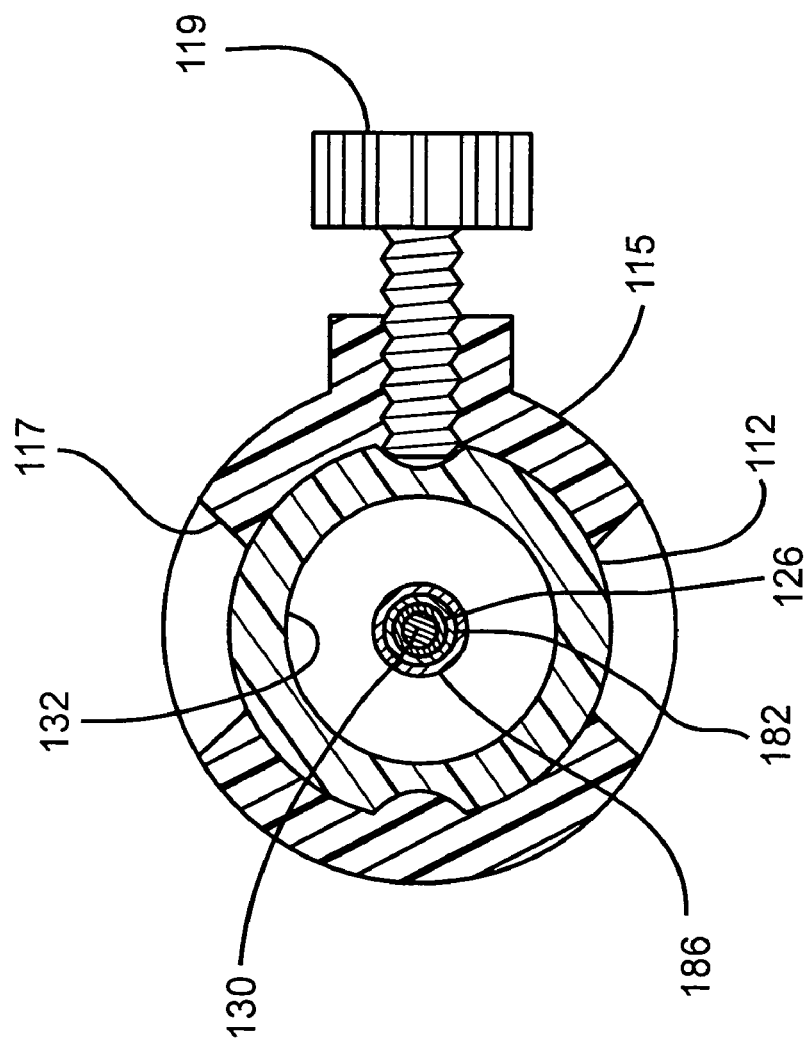
FIG. 6 is a sectional view of the handle illustrated in FIG. 5 taken along line 6—6.

FIGS. 5 and 6 illustrate a handle 110 according to another embodiment of the invention. The handle 110 of this embodiment is identical to the handle of the embodiment described above, except as detailed below. Thus, like reference numbers in FIGS. 5 and 6 refer to similar features and/or components of the embodiment described above and illustrated in FIGS. 1–3, 3A, 3B, 4, 4A, and 4B. FIG. 5 illustrates the handle 110 according to this embodiment in a closed configuration.

In this embodiment, the second outer handle member 120 defines an aperture 111. The aperture 111 is positioned on the second outer handle member 120 such that it is disposed over a portion of a series of gradations 174 disposed on the inner handle member 112. The size and configuration of the aperture 111 can vary, but should be such that the aperture 111 can reveal one or more of the gradations 174 in a meaningful manner.

In this embodiment, the second outer handle member 120 also includes a means for fixing an axial position of the inner handle member 112 relative to the second outer handle member 120. Any suitable means for fixing an axial position between two slideably engaged components can be used. For example, a selectively engageable member that extends through a thickness of the second outer handle member 120 can be used as the means for fixing. The selectively engageable member can be withdrawn from the thickness or advanced through the thickness to engage the inner handle member 112. When disposed through the thickness and in contact with the inner handle member 112, the axial position of the inner handle member 112 relative to the second outer handle member 120 becomes fixed. That is, further axial movement of the second outer handle member 120 along the inner handle member 112 is hindered because of the contact between the inner handle member 112 and the selectively engageable member.

FIG. 5 illustrates a thumb screw 113 that is a suitable selectively engageable member for use as the means for fixing. The thumb screw 113 is readily advanced through a thickness of the second outer handle member 120 and into contact with the inner handle member 112 to fix a relative axial position between the inner 112 and second outer handle 120 members. The second outer handle member 120 provides a thread that interacts with a complimentary thread on the thumb screw 113 to allow its extension into and out of the thickness of the second outer handle member 120.

In this embodiment, a slideable member 115 is also disposed on the inner handle member 112. The slideable member 115 can be a locking member that is slideably disposed on the inner handle member 112. The slideable member 115 can include structural adaptations that allow it to be locked at any of a plurality of positions on the inner handle member 112. For example, the slideable member 115 can include a means for fixing as described above, such as a thumb screw 119 as described above for the second outer handle member 120. The slideable member 115 provides a movable stop that limits movement of the first outer handle member 118 along the inner handle member 112. This stop, therefore, limits the movement of the stylet 126, which is attached to the first outer handle member 118, relative to the sheath 122. By locking the slideable member 115 at a desired position along the inner handle member 112, which may be indicated by a gradation 170, a user of the handle 110 can set a maximum length by which the stylet 126 can extend beyond the sheath 122. Thus, a user can move the first outer handle member 118 along a span of the inner handle member 112 between the fully retracted position and the position at which the slideable member 115 is locked. This span can be a limited portion of the inner handle member 112 along which the first outer handle member can be move, and the precise length of the span depends on the position at which the slideable member 115 is locked. In turn, the chosen position for the slideable member 115 will depend on the desired maximum extension length of the stylet 126 relative to the sheath 122.

To facilitate the positioning of the slideable member 115 at desired locations on the inner handle member 112, the slideable member 115 can define an aperture 117 that reveals an underlying portion of the inner handle member 112, which may include one or more gradations 170. The aperture 117 can take any suitable size, shape, and configuration, but should be adapted to reveal an underlying portion of the inner handle member in a meaningful manner, such as at least one complete gradation 170. As illustrated in FIGS. 5 and 6, the slideable member 115 can comprise a collar that is circumferentially disposed around the inner handle member 112 and between the first 118 and second 120 outer handle members.

Figure 7:
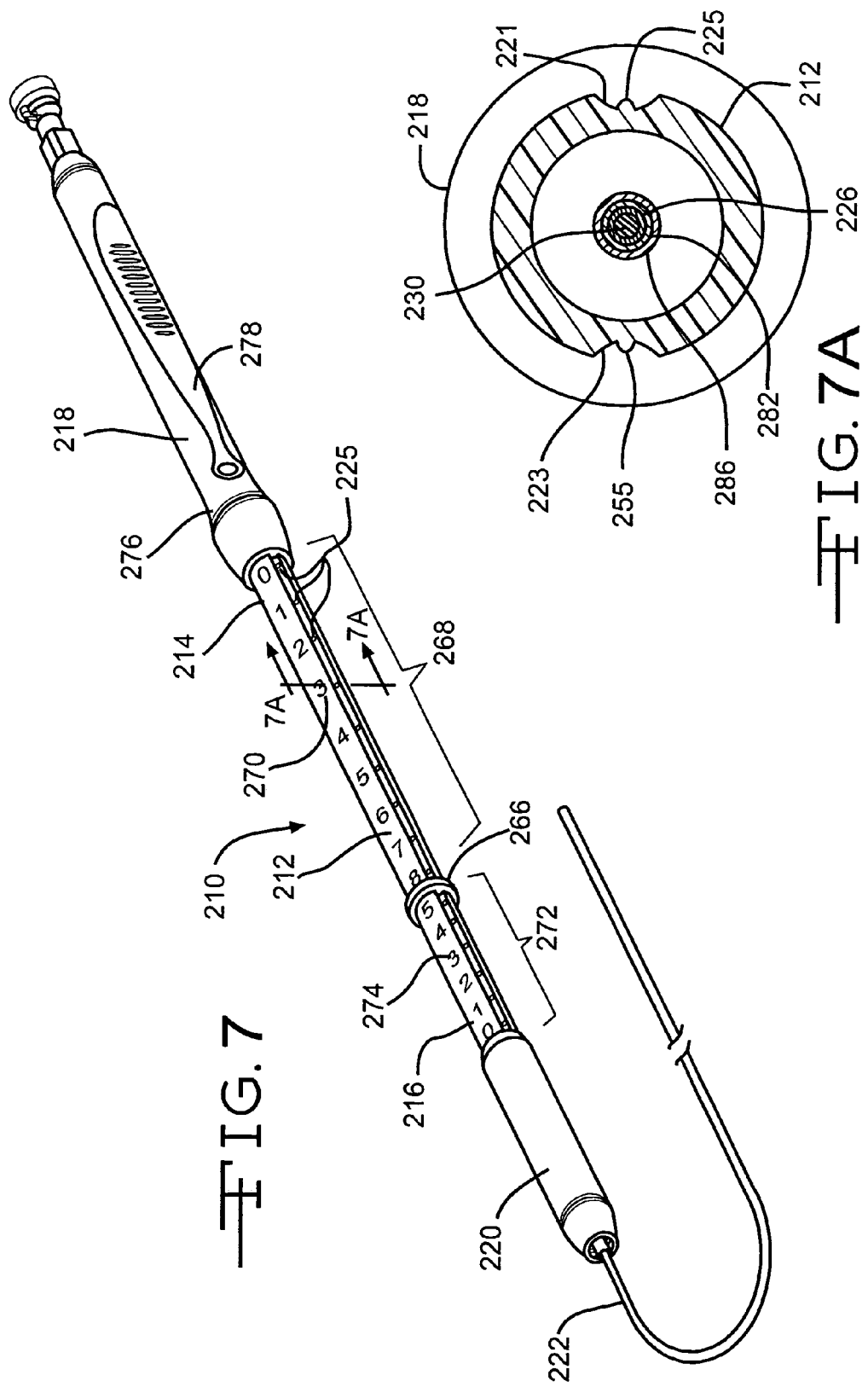
FIG. 7 is a perspective view of a handle according to another embodiment of the invention.

FIGS. 7 and 7A illustrate a handle 210 according to another embodiment of the invention. The handle 210 according to this embodiment is identical to the handle of the first embodiment described above, except as detailed below. Thus, like reference numbers in FIGS. 7 and 7A refer to similar features and/or components of the embodiment described above and illustrated in FIGS. 1–3, 3A, 3B, 4, 4A, and 4B. FIG. 7 illustrates the handle according to this embodiment in an open configuration.

In this embodiment, the inner handle member 212 defines first 221 and second 223 races. One or both of the races 221, 223 include a plurality of stops 225 that define discrete positions on the handle member at which another component, such as the outer handle members 218, 220 or another slideably attached member, can be disposed. In this embodiment, the stops 225 comprise projections defined by the inner handle member 212 and disposed in the races 221, 223. The stops 225 can also comprise separately attached members disposed in the races 221, 223.

The stops 225 temporarily stop slideable movement of a component over the inner handle member 212, but do not halt such movement completely. Rather, the stops 225 simply provide resistance that can be overcome by additional force to produce continued slideable movement of the component along the inner handle member 212. The slideable component can interact with the stops 225 to produce a sound when the slideable component is moved along the inner handle member 212. This production of a sound can provide additional feedback of an operator of the handle 210 that indicates relative position of various components of the handle 210. The slideable components that interact with the stops 225 in this manner could be one or both of the outer handle members 218, 220, or any other slideable component disposed on the inner handle member 212, such as the slideable member described above in relation to the embodiment illustrated in FIGS. 5 and 6.

The stops 225 can be positioned in any suitable arrangement and configuration on the inner handle member 212. As best illustrated in FIG. 7, the stops 225 can be disposed adjacent each gradation 270 in a series of gradations 268 disposed on the inner handle member 212. Also, a first set of stops 225 can be disposed on one portion of the inner handle member 212 while a second set of stops 225 can be disposed on a second portion of the inner handle member 212. For example, as illustrated in FIG. 7, a first set of stops 225 can be disposed adjacent the gradations 270 of a first series 268 of gradations, and a second set of stops 225 can be disposed adjacent gradations 274 of a second series 272 of gradations.

In this embodiment, the inner handle member can define any suitable number of races, and one or more of the races can include stops 225.

Figure 8:
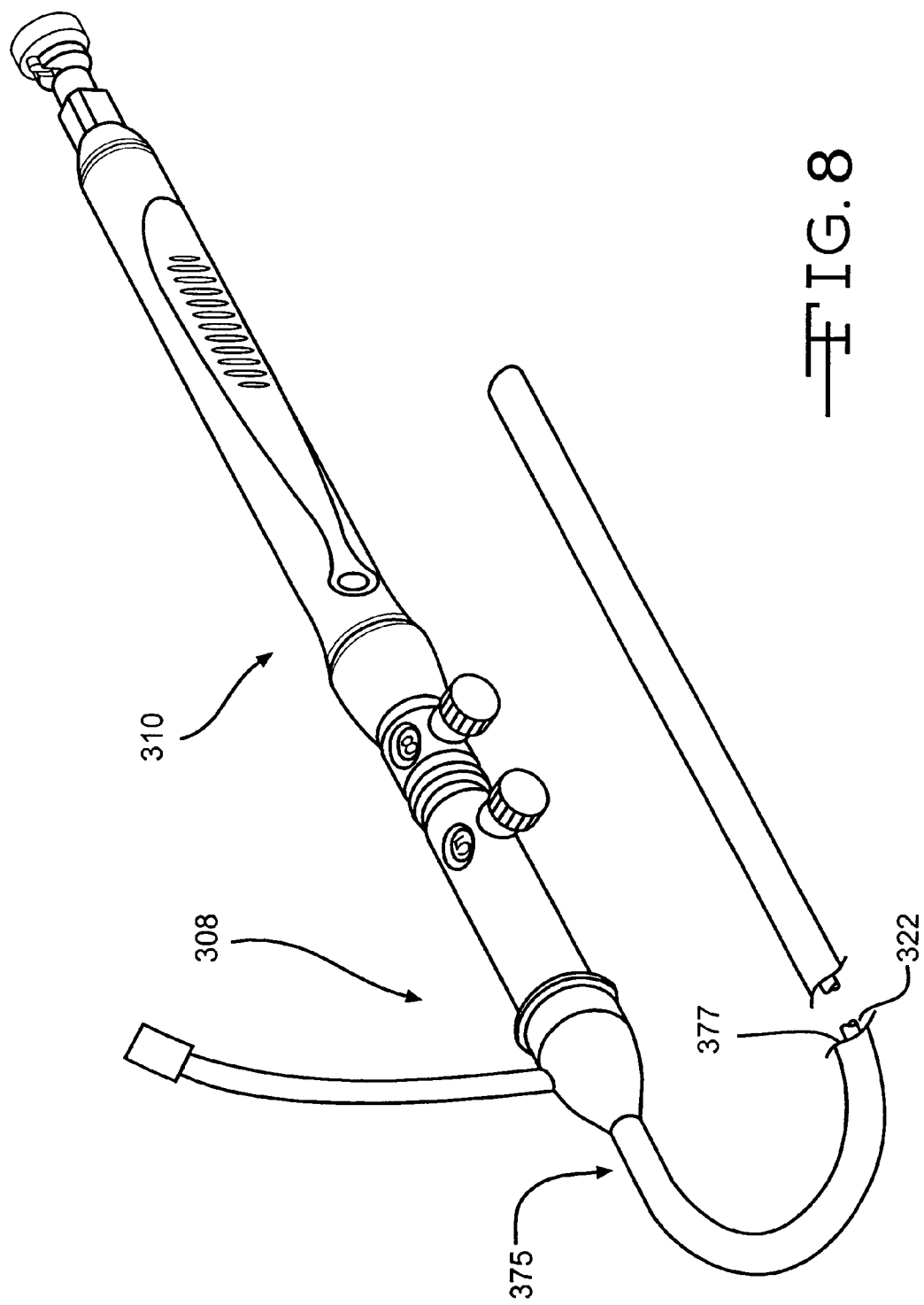
FIG. 8 is a perspective view of a medical device assembly according to one embodiment of the invention.

FIG. 8 illustrates a medical device assembly 308 according to another embodiment of the invention. The medical device assembly 308 comprises a handle 310 according to any embodiment of the invention. The handle 310 is attached to a medical device 375. The medical device 375 defines a working lumen 377. The sheath 322 of the handle 310 is attached to the inner handle member of the handle 310 and axially extends beyond the distal end of the inner handle member and into the working lumen 377 of the medical device 375. The attachment of the handle 310 to the medical device 375 can be accomplished in any suitable manner, including a connector disposed on the second outer handle member 320 as described above.

A suitable medical device 375 for use in the medical device assembly 308 according to the invention comprises an endoscope.

The forgoing detailed description provides exemplary embodiments of the invention and includes the best mode for practicing the invention. These embodiments are intended only to serve as examples of the invention, and not to limit the scope of the invention in any manner.

We claim:

1. A handle for a medical device, comprising:
   an inner handle member having proximal and distal end portions, the proximal and distal end portions being separated by a stop;
   a first outer handle member slideably disposed on the proximal end portion of the inner handle member proximally of the stop;
   a second outer handle member slideably disposed on the distal end portion of the inner handle member distally of the stop;
   an elongate sheath attached to the inner handle member and axially extending beyond the distal end, the sheath defining a sheath lumen; and
   a stylet attached to the first outer handle member and disposed in the sheath lumen.

2. A handle according to claim 1, further comprising a connector on the second outer handle member, the connector having adaptations to connect said handle to said medical device.

3. A handle according to claim 1, wherein the inner handle member defines a handle lumen.

4. A handle according to claim 3, wherein the stylet is disposed in the handle lumen and extends into the sheath lumen.

5. A handle according to claim 1, further comprising means for fixing an axial position of the inner handle member relative to the second outer handle member.

6. A handle according to claim 5, wherein the means for fixing comprises an engaging member extending through a thickness of the second outer handle member.

7. A handle according to claim 6, wherein the engaging member comprises a thumbscrew.

8. A handle according to claim 1, wherein the stop is affixed to the inner handle member and is configured to prevent axial movement of the first outer handle member into the distal end portion of the inner handle member, and prevent axial movement of the second outer handle member into the proximal end portion of the inner handle member.

9. A handle according to claim 8, wherein the stop comprises a projection defined by the inner handle member.

10. A handle according to claim 9, wherein the stop comprises a circumferential projection.

11. A handle according to claim 1, further comprising a first series of gradations disposed on the inner handle member.

12. A handle according to claim 11, wherein each gradation of the first series of gradations corresponds to a predetermined length by which the stylet extends axially beyond a distal end of the sheath.

13. A handle according to claim 11, further comprising a second series of gradations disposed on the inner handle member.

14. A handle according to claim 13, wherein each gradation of the first series of gradations corresponds to a predetermined first length by which the stylet extends axially beyond a distal end of the sheath, and each gradation of the second series of gradations corresponds to a predetermined second length by which the sheath extends axially beyond a distal end of the second outer handle member.

15. A handle according to claim 1, further comprising a slideable member disposed on the inner handle member and adapted to be locked on the inner handle member.

16. A handle according to claim 15, wherein the slideable member is disposed between the first and second outer handle members.

17. A handle according to claim 15, wherein the slideable member comprises a mechanical stop that limits axial movement of the first outer handle member along the inner handle member.

18. A handle according to claim 15, further comprising a series of gradations disposed on the inner handle member, wherein the slideable member defines an aperture disposed over a portion of the series of gradations.

19. A handle according to claim 18, wherein each gradation of the series of gradations corresponds to a predetermined length by which the stylet extends axially beyond a distal end of the sheath.

20. A handle according to claim 15, wherein the inner handle member comprises a plurality of stops that define discrete positions on the inner handle member at which the slideable member can be disposed.

21. A handle according to claim 20, wherein the slideable member interacts with the plurality of stops to produce a sound when the slideable member is moved axially along the inner handle member.

22. A handle for a medical device comprising:
an inner handle member having a proximal end portion and distal end portion separated by a stop;
first and second outer handle members slideably disposed on the inner handle member, the first outer handle member being slideably disposed along the proximal end portion proximally of the stop, and the second outer member being slideably disposed along the distal end portion distally of the stop;
an elongate sheath attached to the inner handle member and defining a sheath lumen;
a stylet attached to the first outer handle member and disposed in the sheath lumen; and
a series of gradations disposed on the inner handle member, each gradation of the series of gradations corresponding to a predetermined length by which the stylet extends axially beyond a distal end of the sheath.

23. A handle according to claim 22, wherein the series of graduations is disposed along the proximal end portion of the inner handle member proximally of the stop, and further comprising a second series of gradations, each gradation of the second series of gradations corresponding to a predetermined second length by which the sheath extends axially beyond a distal end of the second outer handle member, the second series of gradations being disposed along the distal end portion of the inner handle member distally of the stop.

24. A handle for a medical device comprising:
an inner handle member having proximal and distal ends and defining a handle lumen, the proximal and distal ends being separated by a stop connected to the inner handle member;
a first outer handle member slideably disposed on the proximal end proximally of the stop;
a second outer handle member slideably disposed on the distal end distally of the stop;
an elongate sheath attached to the inner handle member and axially extending distally beyond the distal end, the sheath defining a sheath lumen;
a stylet attached to the first outer handle member, the stylet extending through the handle lumen and into the sheath lumen;
a first series of gradations disposed on the inner handle member, each gradation of the first series of gradations corresponding to a predetermined first length by which the stylet extends axially beyond a distal end of the sheath; and
a second series of gradations disposed on the inner handle member, each gradation of the second series of gradations corresponding to a predetermined second length by which the sheath extends axially beyond a distal end of the second outer handle member.

25. A medical device assembly comprising:
a medical device defining a working lumen; and;
a handle, the handle comprising an inner handle member having proximal and distal ends separated by a stop, a first outer handle member slideably disposed on the proximal end, a second outer handle member slideable disposed on the distal end, an elongate sheath attached to the inner handle member and axially extending beyond the distal end and into the working lumen of the medical device, the sheath defining a sheath lumen, and a stylet attached to the first outer handle member and disposed in the sheath lumen.

26. A medical device assembly according to claim 25, wherein the medical device comprises an endoscope.

27. A medical device assembly according to claim 25, wherein the second outer handle member is attached to the medical device.

28. A medical device assembly according to claim 26, further comprising a first series of gradations disposed on the inner handle member, wherein each gradation of the first series of gradations corresponds to a predetermined length by which the stylet extends axially beyond a distal end of the sheath.

29. A medical device assembly according to claim 27, further comprising a second series of gradations disposed on the inner handle member, wherein each gradation of the second series of gradations corresponds to a predetermined second length by which the sheath extends axially beyond a distal end of the working lumen.

* * * * *